United States Patent
Dombou et al.

[11] Patent Number: 5,294,546
[45] Date of Patent: Mar. 15, 1994

[54] METHOD FOR PRODUCTION OF A GROWTH FACTOR FOR BIFIDOBACTERIUM SP.

[75] Inventors: Munehiko Dombou; Isao Tomioka; Ryoichi Tsurutani; Senji Kitabatake; Hiroshi Nakajima, all of Kyoto, Japan

[73] Assignee: Unitika Ltd., Hyogo, Japan

[21] Appl. No.: 799,881

[22] Filed: Nov. 29, 1991

Related U.S. Application Data

[63] Continuation of Ser. No. 101,603, Sep. 28, 1987, abandoned.

[30] Foreign Application Priority Data

Sep. 27, 1986 [JP] Japan .................. 61-229223
Jun. 4, 1987 [JP] Japan .................. 62-142106

[51] Int. Cl.$^5$ ............................... C12P 19/04
[52] U.S. Cl. ............................ 435/101; 435/207; 435/921; 435/922; 435/923; 435/924; 435/938; 435/944; 435/174
[58] Field of Search ........... 435/101, 207, 921, 922, 435/923, 924, 938, 944

[56] References Cited

U.S. PATENT DOCUMENTS

| | | | |
|---|---|---|---|
| 3,859,167 | 1/1975 | Ogino et al. | 435/119 |
| 4,275,158 | 6/1981 | Taoka et al. | 435/136 |
| 4,375,515 | 3/1983 | Patel et al. | 435/189 |
| 4,590,160 | 5/1986 | Nishihashi et al. | 435/78 |

FOREIGN PATENT DOCUMENTS 0251896 12/1985 Japan .
2080330 of 0000 United Kingdom .

OTHER PUBLICATIONS

Patent Abstracts of Japan, vol. 11, No. 85 (C-410), Mar. 14, 1987.
Data Commonwealth Agriculture Bank, abstract no. 84389437; C. C. Cheny et al.: "Associative relationships between Bifidobacteria and Lactobacilli in milk".
Patent Abstracts of Japan, vol. 8, No. 24 (C-208) (1461), Feb. 2, 1984.
Canadian Journal of Chemistry, vol. 42, 1964, pp. 1341-1344, Ottawa, Canada; Paj Gorin et al.: "The Structures of Galactosyl-Lactose and Galactobiosyl-Lactose Produced from . . . Singularis".
Patent Abstracts of Japan, vol. 7, No. 201 (C-184) (1346), Sep. 6, 1983.
Patent Abstracts of Japan, vol. 12, No. 70 (C-497) Mar. 4, 1988.
Yeast: Characteristics & Identification, Barnett et al., Cambridge Univ Press, Cambridge, 1983.
Gorin, P.; J. Spencer & H. Phaff. "The structures of galactosyl-lactose and galactobiosyl-lactose produced from lactose by Sporobolomyces singularis" *Canadian Journal of Chemistry* 42 (1964) pp. 1341-1344.
Deavin et al., "The production of alginic acid by *Azotobacter vinelandii* in batch and continuous culture" in *Extracellular Microbioal Polysaccharides*, American Chemical Society, New York, 1977, pp. 14-17.
Stanbury, P. and A. Whitaker, *Principles of Fermentation Technology*, Pergamon Press, N.Y., 1984, pp. 13-14.

*Primary Examiner*—Douglas W. Robinson
*Assistant Examiner*—Jean C. Witz
*Attorney, Agent, or Firm*—Sughrue, Mion, Zinn, Macpeak & Seas

[57] ABSTRACT

A method of producing a growth promoting factor for Bifidobacterium species from lactose which comprises contacting lactose with resting cells of a lactose-utilizing yeast strain having activity to rearrange lactose to galacto-oligosaccharides.

14 Claims, No Drawings

METHOD FOR PRODUCTION OF A GROWTH FACTOR FOR BIFIDOBACTERIUM SP.

This is a continuation of application Ser. No. 07/101,603 filed Sep. 28, 1987, now abandoned.

FIELD OF THE INVENTION

This invention relates to a method of producing a growth promoting factor for Bifidobacterium species (hereinafter referred to as bifidobacteria).

BACKGROUND OF THE INVENTION

It is known that bifidobacteria are useful inhabitants of the human intestine and it is known that as they are colonized there, these bacteria produce lactic acid, acetic acid and formic acid to lower the pH in the intestinal tract and thereby tend to preclude local settlement of pathogenic organisms. Compounds having activity to encourage the growth and proliferation of these useful bifidobacteria have been utilized as additives incorporated into various foods such as evaporated milk, beverages and so on.

Much research has been undertaken into growth promoting factors for bifidobacteria (hereinafter referred to as bifidus factors) and as such factors, there have been reported lactulose, fructo-oligosaccharides, galacto-oligosaccharides of the general formula Gal—(Gal)$_n$—Glc (wherein Gal is a galactose residue, Galc is a glucose residue, and n is a whole number of 1 to 4), carrot extract, N-acetyllactosamine, and so on.

For the production of a galacto-oligosaccharide from lactose using an enzymatic or microbial technique, there are known a process which employs β-galactosidase produced by *Aspergillus oryzae* (Japanese Patent Publication No.20266/83; corresponding U.S. Pat. No. 4,435,389), a process which comprises growing a strain of Bacillus sp. in a lactose-containing medium and harvesting the bifidus factor from the culture broth (Japanese Patent Application (OPI) No. 115796/81 (the term "OPI" as used herein refers to a "published unexamined Japanese patent application"), a process which comprises growing a yeast of the genus Cryptococcus in a lactose-containing medium and harvesting a galacto-oligosaccharide from the broth (Japanese Patent Application (OPI) No. 251896/85), a process in which a galacto-oligosaccharide is produced using the lactase derived from *Saccharomyces fragilis* (Agricultural and Food Chemistry 5, 130 k, (1957)), a process in which a strain of *Sporobolomyces singularis* is cultured in a lactose-containing medium to produce a galacto-oligosaccharide in the broth (Canadian Journal of Chemistry 42, 1341, (1964)), a process which comprises growing a strain of *Penicillium chrysogenum* in a lactose-containing medium to produce a galacto-oligosaccharide in the broth (Tetrahedron 9, 125, (1960)), a process in which a galacto-oligosaccharide is produced by using a β-galactosidase of Lactobacillus origin (Journal of Dairy Science 64, 185, (1981)), and a process which employs the β-galactosidase derived from *Bacillus circulans* to produce a galacto-oligosaccharide (Agricultural Biological Chemistry 48, 3053, (1984)), among others.

The foregoing processes for producing bifidus factors from lactose may be roughly classified into those employing enzymes extracted from the microbial cells and those in which a certain strain of microorganism is cultured in a lactose-containing medium and the resulting galacto-oligosaccharide is harvested from the culture broth. Of these two groups of processes, the processes employing the enzymes extracted from microbial cells of course call for the extraction of enzymes which is labor- and time-consuming. Moreover, these processes entail hydrolysis of lactose as well as of the desired galacto-oligosaccharide and the consequent accumulation of glucose and galactose as by-products of the reaction, thus causing a waste of the starting material lactose and leading to a reduced yield of the galacto-oligosaccharide.

On the other hand, the processes involving the production of galacto-oligosaccharides in culture media are disadvantageous in that because the cells grow and multiply, other microbial secretions are also accumulated in the media and interfere with the separation and purification of galacto-oligosaccharides and also in that the desired galacto-oligosaccharides must be separated from the materials incorporated in the medium, namely the nitrogen sources, vitamins, trace elements and so on which are necessary or useful for the growth of bacteria.

SUMMARY OF THE INVENTION

The object of this invention is to provide a method of producing a bifidus factor with high efficiency. The intensive research conducted by the present inventors to overcome the above-mentioned disadvantages led to the finding that resting cells of a lactose-utilizing yeast can be advantageously utilized in the production of bifidus factors.

This invention is, therefore, directed to a method of producing a bifidus factor from lactose which comprises contacting lactose with resting cells of a yeast strain which is able to utilize lactose and arrange lactose to form galacto-oligosaccharides.

In accordance with this invention, the procedure of extracting the enzyme from cultured cells can be omitted and the cells grown in a conventional medium can be simply separated by the conventional techniques such as centrifugation, filtration or the like and used as they are. Moreover, as the yeast cells are used as a so-called enzyme bag, all that is required is to add lactose thereto as the enzymatic reaction substrate.

Furthermore, in accordance with this invention, the wasteful decomposition of lactose is not induced, but rather the rearrangement reaction of lactose to form galacto-oligosaccharides alone takes place selectively so that not only the yield of the bifidus factor is improved but the yeast cells can be re-used again and again, thus assuring an efficient production of the bifidus factor.

DETAILED DESCRIPTION OF THE PREFERRED EMBODIMENT

The yeast to be employed in accordance with this invention is any strain capable of utilizing lactose and having lactose rearrangement activity. Preferred are lactose-utilizing yeasts belonging to the genera of Rhodotorula, Pichia, Sporobolomyces, Kluyveromyces, Debaryomyces, Candida, Torulopsis, Cryptococcus, Trichosporon, Lipomyces, Bullera, and Brettanomyces.

Specific strains of such yeasts include *Rhodotorula lactosa* IFO 1423, IFO 1424, *Cryptococcus laurentii* IFO 0372, IFO 0384, IFO 0930, IFO 1376, IFO 1487, *Pichia polymorpha* IFO 1166, IFO 1357, *Sporobolomyces singularis* ATCC 24193, *Kluyveromyces lactis* IFO 0433, IFO 0648, IFO 1090, IFO 1267, IFO 1903, *Debaryomy-*

*ces cantarellii* IFO 1189, IFO 1363, IFO 1716, IFO 1717, *Candida curvata* IFO 0732, IFO 1159, *Lipomyces lipofer* IFO 0673, IFO 1288, *Torulopsis candida* IFO 0380, IFO 0664, IFO 0768, *Trichosporon pullulans* IFO 0114, *Bullera alba* IFO 1192, *Brettanomyces anomalus* IFO 0642.

Particularly, this invention is preferably conducted using *Lipomyces starkeyi* and, most desirably, a biologically pure culture of *Lipomyces* NKD-14 (FERM P-8948, Intenational Accession No. BP-1456 under Budapest Treaty) which does not cause a wasteful decomposition of substrate lactose but is selectively conductive to a rearrangement reaction of lactose to give a high yield of the desired bifidus factor.

Lipomyces NKD-14 was isolated from the soil sample collected at the Atsukawa hotspring resort, Shizuoka Prefecture, Japan and its mycological characteristics have been investigated for taxonomic identification in accordance with the description and procedures set forth in J. Lodder, The Yeasts (1984) and H. Iizuka and S. Goto, Methods for Taxonomic Identification of Yeasts (1969). The mycological characteristics of Lipomyces NKD-14 are set forth below.

(1) Cultural characteristics (a) My broth (Glucose 10 g/l, Peptone 5 g/l, Yeast extract 3 g/l, Malt extract 3 g/l)

Cultured at 30° C. for 3-7 days, the cells measure $(3.75-5) \times 5\mu$ being spherical or ellipsoidal. The capsule is formed. The oidium not formed. Multiplication by multilateral budding.

(b) My agar (Glucose 10 g/l, Peptone 5 g/l, Yeast extract 3 g/l, Malt extract 3 g/l, Agar 15 g/l)

Cultured at 30° C. for 4 days, colonies are cream in color and opaque. The consistency of the colonies is mucoid.

(c) Cornmeal agar slide

Culture at 30° C. Neither mycelia nor pseudo-mycelia are observed.

(2) Formation of ascospores

On a nitrogen-free medium, 8 to 10 spores are formed.

(3) Formation of ballistospores

On an MY agar plate, ballistospores are not formed.

(4) Physiological characteristics (a) Optimum range for growth

Good growth at 26°-32° C. and fair growth even at 24°-35° C. Good growth at pH 5-7.

(b) Range of growth

No growth under 5° C. or over 37° C. No growth under pH 2 or over pH 10.

(c) Nitrates not utilized
(d) Lipids not hydrolyzed
(e) Urea not hydrolyzed
(f) Gelatin not liquefied
(g) Carotinoid pigment not produced
(h) Starch-like substance produced
(i) Vitamin requirements No growth on vitamin-deficient media (j) Arbutin hydrolyzed (5) Fermentation of sugars The symbol "—" denotes no fermentation.

|  |  |
|---|---|
| D-Glucose | — |
| D-Galactose | — |
| Lactose | — |
| Sucrose | — |
| Maltose | — |
| Raffinose | — |

(6) Assimilation of carbon sources

The symbol "+" denotes good assimilation; "±" weak assimilation; "—" no assimilation.

|  |  |
|---|---|
| D-Glucose | + |
| D-Galactose | + |
| L-Sorbose | + |
| Maltose | + |
| Sucrose | + |
| D-Ribose | ± |
| L-rhamnose | + |
| Ethanol | + |
| Erythritol | + |
| Trehalose | + |
| Melibiose | + |
| Melezitose | + |
| Inulin | + |
| Soluble starch | + |
| D-Xylose | + |
| L-Arabinose | + |
| D-Arabinose | + |
| D-Mannitol | + |
| α-Methyl-D-glucoside | + |
| DL-Lactic acid | — |
| Succinic acid | ± |
| Citric acid | — |
| Inositol | + |
| Dextrin | + |

Reference of the above micological characteristics to J. Lodder: The Yeasts (1984) revealed that the strain belongs to *Lipomyces starkeyi* but that it differs from the known strains. Therefore, it was designated as Lipomyces NKD-14 and deposited at the Fermentation Research Institute, the Agency of Industrial Science and Technology Ministry of International Trade and Industry, Japan, on Sep. 1, 1986 under the accession number of FERM P-8948 (conformity with the International Accession Number BP-1456 under Budapest Treaty).

There is no particular limitation on the conditions for production of yeast cells. Thus, resting cells having high bifidus factor-synthesizing activity can be obtained by culturing the strain in a lactose-containing medium. Alternatively, the strain may be grown in a medium containing glucose, sorbitol, maltose, sucrose, spent molasses, etc. as carbon sources until sufficient growth is obtained, and after addition of lactose, the cultivation continued until a sufficient titer of β-galactosidase is induced. After the above procedure, the cells can be harvested by the conventional procedures such as centrifugation and filtration. The nitrogen sources which can be used for cultivation include various organic nitrogenous materials such as peptone, casein, corn steep liquor, meat extract, yeast extract, etc. and various inorganic nitrogen compounds such as ammonium sulfate, ammonium chloride, urea and so on.

The strain can be cultured by any of the known cultural methods such as stationary culture, aerobic submerged culture, shake culture and so on using a conventional liquid or solid medium. The cells harvested by centrifugation or filtration can be used as such as the reaction catalyst without further treatment. As an alternative, the cells may be used in an immobilized state by an appropriate immobilization procedure.

There is no particular limitation on the method of immobilization. Thus, entrapment in acrylamide gel, calcium alginate gel, etc., crosslinking by the intercellular crosslinking method using glutaraldehyde, toluene diisocyanate, etc., immobilization by coupling with Dowex 50 (Dow Chemical), CM-cellulose, P-cellulose, DEAE-cellulose, ECTEOLA-cellulose (Whatman), etc., and immobilization by adsorption on saw dust, etc.

may be mentioned. The thus-immobilized yeast cells can be used by packing them into a columnar reactor. The free or immobilized yeast cells can also be suspended in a membrane-type reaction vessel so that the reaction product alone is continuously withdrawn from the reaction vessel.

The concentration of lactose to be treated with the yeast cells in this invention is not less than 1%(w/v), preferably not less than 5%(w/v) and still more desirably not less than 10%(w/v). The pH of the reaction system is preferably in the range of pH 3 to 9, and more desirably pH 5 to 7. Of course, it is preferable to use a pH at which the yeast cells are scarsely lyzed and display the maximal bifidus factor-synthesizing activity.

If necessary, buffer solutions may be used. The temperature to be used in such cases is 10° to 50° C. and is preferably in the range of 25° to 45° C.

When the reaction is conducted under such conditions, the bifidus factor oligosaccharide is produced. After completion of this reaction, the cells are removed by filtration, centrifugation or decantation as required to obtain a filtrate containing the oligosaccharide. Generally, this filtrate is desalted by passage through an ion exchange resin and when a pure oligosaccharide is to be produced, the eluate is further subjected to adsorption chromatography using activated carbon, gel filtration and so on.

The following reference and working examples are further illustrative of this invention.

Unless otherwise indicated, all ratios, percents, etc. are by weight.

REFERENCE EXAMPLE 1

Ten 500 ml conical flasks were filled with 100 ml portions of a medium of the following composition and sterilized by autoclaving.

| Lactose | 5 g |
|---|---|
| Ammonium sulfate | 0.2 g |
| Yeast extract | 0.02 g |
| $KH_2PO_4$ | 0.08 g |
| $Na_2HPO_4.12H_2O$ | 0.03 g |
| $MgSO_4.7H_2O$ | 0.002 g |
| Water | 100 ml |
| pH | 5.6 |

Each flask was then inoculated with a loopful of *Rhodotorula lactosa* IFO 1423 and incubated on a rotary shaker at 30° C. for 3 days. The resulting broth was centrifuged to give 5.2 g of moist cells.

REFERENCE EXAMPLE 2

Ten 500 ml conical flasks were filled with 100 ml portions of a medium of the following composition and autoclaved.

| Lactose | 5 g |
|---|---|
| Polypeptone | 0.5 g |
| Yeast extract | 0.3 g |
| Water | 100 ml |
| pH | 5.6 |

Each flask was then inoculated with a loopful of *Cryptococcus laurentii* IFO 0372 and incubated on a rotary shaker at 30° C. for 2 days. The resulting broth was centrifuged to give 7.5 g of moist cells.

REFERENCE EXAMPLE 3

Ten flasks containing the same medium as Reference Example 1 were respectively inoculated with a loopful of *Pichia polymorpha* IFO 1166 and incubated on a rotary shaker at 30° C. for 3 days. The resulting broth was centrifuged to give 5.5 g of moist cells.

REFERENCE EXAMPLE 4

Ten flasks containing the same medium as Reference Example 2 were respectively inoculated with a loopful of *Sporobolomyces singularis* ATCC 24193 and incubated on a rotary shaker at 30° C. for 2 days. The resulting broth was centrifuged to give 3.2 g of moist cells.

REFERENCE EXAMPLE 5

Ten flasks containing the same medium as Reference Example 2 were respectively inoculated with a loopful of *Kluyveromyces lactis* IFO 0433 and incubated on a rotary shaker at 30° C. for 2 days. The resulting broth was centrifuged to give 5.3 g of moist cells.

REFERENCE EXAMPLE 6

Ten flasks containing the same medium as Reference Example 2 were respectively inoculated with a loopful of *Debaryomyces cantarellii* IFO 1189 and incubated on a rotary shaker at 30° C. for 2 days. The resulting broth was centrifuged to give 3 g of moist cells.

REFERENCE EXAMPLE 7

Ten flasks containing the same medium as Reference Example 2 were respectively inoculated with a loopful of *Candida curvata* IFO 0732 and incubated on a rotary shaker at 30° C. for 3 days. The resulting broth was centrifuged to give 2.5 g of moist cells.

REFERENCE EXAMPLE 8

Ten flasks containing the same medium as Reference Example 2 were respectively inoculated with a loopful of *Torulopsis candida* IFO 0380 and incubated on a rotary shaker at 30° C. for 2 days. The resulting broth was centrifuged to give 3.2 g of moist cells.

REFERENCE EXAMPLE 9

Ten flasks containing the same medium as Reference Example 2 were respectively inoculated with a loopful of *Trichosporon pullulans* IFO 0114 and shaker at 30° C. for 2 days. The resulting broth was centrifuged to give 3.1 g of moist cells.

REFERENCE EXAMPLE 10

Ten flasks containing the same medium as Reference Example 2 were respectively inoculated with a loopful of *Bullera alba* IFO 1192 and incubated on a rotary shaker at 30° C. for 3 days. The resulting broth was centrifuged to give 2.8 g of moist cells.

REFERENCE EXAMPLE 11

Ten 500 ml conical flasks were filled with 100 ml portions of a medium of the following composition and autoclaved.

| Glucose | 2 g |
|---|---|
| Polypeptone | 0.2 g |
| Yeast extract | 0.1 g |
| Water | 100 ml |

| | |
|---|---|
| -continued | |
| pH | 5.6 |

Each flask was then inoculated with a loopful of *Brettanomyces anomalus* IFO 0642 and incubated on a rotary shaker at 30° C. for 2 days. Then, sterile lactose was added at the level of 2% and the incubation was further continued for 1 day. The resulting broth was centrifuged to give 3.9 g of moist cells.

REFERENCE EXAMPLE 12

Ten flasks containing the same medium as Reference Example 2 were each inoculated with a loopful of *Lipomyces lipofer* IFO 0673 and incubated on a rotary shaker at 30° C. for 2 days. The resulting broth was centrifuged to give 3.5 g of moist cells.

REFERENCE EXAMPLE 13

A 30-liter jar fermentater was charged with the following medium.

| | |
|---|---|
| Lactose | 400 g |
| Ammonium sulfate | 40 g |
| $KH_2PO_4$ | 10 g |
| $Na_2HPO_4 \cdot 12H_2O$ | 10 g |
| $MgSO_4 \cdot 7H_2O$ | 10 g |
| Yeast extract | 20 g |
| Tap Water | 20 l |

After sterilization, the fermenter was inoculated with 1 liter of a seed culture (30° C., 24 hrs.) of Lipomyces NKD-14 (FERM P-8948) and incubated under the conditions of pH 6.5, 30° C., air sparging 20 l/min. and impeller speed 400 r.p.m. for 18 hours. After completion of fermentation, the broth was centrifuged using an α-Laval Model LAPZ 202 centrifuge to give 2.8 kg of moist cells.

REFERENCE EXAMPLE 14

To 50 of the moist cells prepared in the same manner as Reference Example 13 was added 5 g of sodium alginate followed by addition of 200 ml of tap water. The mixture was stirred using a mixer until a homogenous suspension was obtained. Using an injection needle, this suspension was dripped into a 0.2M solution of calcium chloride to give 110 g of beads of calcium alginate-immobilized cells.

REFERENCE EXAMPLE 15

Ten 500 ml Sakaguchi flasks were filled with 100 ml portions of the same medium as Reference Example 13 and sterilized. Then, each flask was inoculated with a loopful of Lipomyces NKD-14 (FERM P-8948) and incubated at 30° C. for 3 days. The resulting broth was centrifuged to give 2.5 g of moist cells.

EXAMPLE 1 AND COMPARATIVE EXAMPLE 1

Ten grams of lactose was added to 5.2 g of the moist cells of *Rhodotorula lactosa* IFO 1423 obtained in Reference Example 1, followed by addition of tap water to make 100 ml. This suspension was adjusted to pH 6.5 and allowed to stand at 30° C. for 3 days.

The suspension was centrifuged to separate the supernatant. Analysis of this supernatant by high performance liquid chromatography (Waters, μ-Bonadapak/$NH_2$, mobile phase: acetonitrile/water=7:3) showed a galacto-oligosaccharide peak at the trisaccharide position as well as a lactose peak.

On the other hand, glucose and galactose which are hydrolysates of lactose were not detected at all. The yield of galacto-oligosaccharide was 40%.

As a control, 200 units of a commercial β-galactosidase derived from *Aspergillus oryzae* (Sigma) was added to a solution of 10 g of lactose in 100 ml of 10 mM acetate buffer (pH 5.5) and the mixture was allowed to stand at 30° C. for 24 hours.

When this mixture was analyzed in the same manner as Example 1, a peak of galacto-oligosaccharide was detected at the trisaccharide position. The substrate lactose was partially hydrolyzed to glucose and galactose. The yield of galacto-oligosaccharide was 19%.

Table 1 shows the sugar composition of the reaction product according to Example 1 in comparison with that of the product according-g to Comparative Example 1.

TABLE 1

| Example No. | Oligosaccharide (%) | Monosaccharide (%) | Lactose (%) |
|---|---|---|---|
| Comparative Example 1 | 19.0 | 60.8 | 20.2 |
| Example 1 | 40.0 | 0 | 60.0 |

EXAMPLE 2

Ten grams of lactose was added to 5 g of the moist cells of *Cryptococcus laurentii* IFO 0372 obtained in Reference Example 2 followed by addition of tap water to make 100 ml. This suspension was adjusted to pH 7.5 and allowed to stand at 30° C. for 2 days.

The reaction mixture was centrifuged and the supernatant was sterilized by autoclaving and freeze-dried. The bifidus activity of the lyophilizate was determined.

As a control, 10 g of lactose was added to 5 g of the moist cells of *Cryptococcus laurentii* IFO 0372 followed by addition of tap water to make 100 ml. The suspension was adjusted to pH 7.5 and immediately subjected to autoclaving, instead of allowing to stand at 30° C. for 2 days, and then lyophilized (the untreated mixture).

For a test for bifidus activity, each of the above lyophilizates was added to Glyörgy's standard medium for Bifidus Pen strain (Japanese Journal of Pediatrics 9, 839, (1956)) at the level of 5%. The medium was then inoculated with the same inoculum size of Bifidus Pen strain and after liquid paraffin was overlayed, anaerobic culture was carried out at 37° C. for 48 hours. The degree of growth of the bifidus strain was determined from the acidity and pH. Acidity was determined by the titration of a sample with a standard solution.

The results are shown in Table 2.

EXAMPLE 3

The procedure of Example 2 was repeated except that 5 g of the moist cells of *Pichia polymorpha* IFO 1166 obtained in Reference Example 3 was employed and the bifidus activity was determined.

The results are set forth in Table 2.

EXAMPLE 4

The procedure of Example 2 was repeated except that 3 g of the moist cells of *Sporobolomyces singularis* ATCC 24193 obtained in Reference Example 4 was employed and the bifidus activity was determined.

The results are set forth in Table 2.

EXAMPLE 5

The procedure of Example 2 was repeated except that 5 g of the moist cells of *Kluyveromyces lactis* IFO 0433 obtained in Reference Example 5 was employed and the bifidus activity was determined.

The results are set forth in Table 2.

EXAMPLE 6

The procedure of Example 2 was repeated except that 2 g of the moist cells of *Debaryomyces cantatrellii* IFO 1189 obtained in Reference Example 6 was employed and the bifidus activity was determined.

The results are set forth in Table 2.

EXAMPLE 7

The procedure of Example 2 was repeated except that 2 g of the moist cells of *Candida curvata* IFO 0732 obtained in Reference Example 7 was employed and the bifidus activity was determined.

The results are set forth in Table 2.

EXAMPLE 8

The procedure of Example 2 was repeated except that 2 g of the moist cells of *Torulopsis candida* IFO 0380 obtained in Reference Example 8 was employed and the bifidus activity was determined.

The results are set forth in Table 2.

EXAMPLE 9

The procedure of Example 2 was repeated except that 3 g of the moist cells of *Trichosporon pullulans* IFO 0114 obtained in Reference Example 9 was employed and the bifidus activity was determined.

The results are set forth in Table 2.

EXAMPLE 10

The procedure of Example 2 was repeated except that 2.5 g of the moist cells of *Bullera alba* IFO 1192 obtained in Reference Example 10 was employed and the bifidus activity was determined.

The results are set forth in Table 2.

EXAMPLE 11

The procedure of Example 2 was repeated except that 3 g of the moist cells of *Brettanomyces anomalus* IFO 0642 obtained in Reference Example 11 was employed and the bifidus activity was determined.

The results are set forth in Table 2.

TABLE 2*

| | Test Medium | | | | | |
|---|---|---|---|---|---|---|
| | Standard Medium Containing the Product of the Invention | | Standard Medium Containing the Untreated Mixture | | Standard Medium | |
| Example No. | Acidity | pH | Acidity | pH | Acidity | pH |
| Example 2 | 0.70 | 5.0 | 0.25 | 5.7 | 0.25 | 5.9 |
| Example 3 | 0.50 | 5.0 | 0.30 | 5.5 | 0.25 | 5.8 |
| Example 4 | 0.47 | 5.2 | 0.30 | 5.5 | 0.24 | 5.8 |
| Example 5 | 0.66 | 5.0 | 0.30 | 5.2 | 0.25 | 5.8 |
| Example 6 | 0.50 | 5.0 | 0.30 | 5.2 | 0.25 | 5.8 |
| Example 7 | 0.70 | 5.0 | 0.30 | 5.3 | 0.24 | 5.8 |
| Example 8 | 0.50 | 5.1 | 0.30 | 5.3 | 0.23 | 5.8 |
| Example 9 | 0.60 | 5.0 | 0.30 | 5.3 | 0.23 | 5.8 |
| Example 10 | 0.55 | 5.2 | 0.30 | 5.3 | 0.23 | 5.8 |
| Example 11 | 0.71 | 4.9 | 0.30 | 5.3 | 0.24 | 5.8 |

*The change of media on incubation in terms of acidity and pH.

It is apparent from Table 2 that the products of this invention have bifidus activity.

EXAMPLE 12

In 4 ml of physiological saline was suspended 1 g of the moist cells of *Lipomyces lipofer* IFO 0673 obtained in Reference Example 12 followed by addition of 750 mg of acrylamide and, as a crosslinking agent, 40 mg, of N,N'-methylenebisacrylamide. Then 0.5 ml of 5% $\beta$-dimethylaminopropionitrile as a polymerization accelerator and 0.5 ml of 2.5% potassium peroxydisulfate as a polymerization initiator were added. The mixture was stirred well and allowed to stand at 30° C. for 30 minutes. The resulting gel was washed with physiological saline to give an immobilized yeast cell preparation.

To the above immobilized yeast cell preparation was added 10 g of lactose, followed by addition of water to make 100 ml. The mixture was adjusted to pH 7.5 and allowed to stand at 30° C. for 24 hours. The mixture was then centrifuged to give a supernatant free of the immobilized cells. This supernatant was lyophilized.

As a control, the mixture was not allowed to stand at 30° C. for 24 hours but immediately centrifuged and the supernatant was lyophilized. This lyophilizate (untreated mixture) was used as a control sample.

These lyophilizates were assayed for bifidus activity in the same manner as Example 2 and the degree of multiplication of the bifidus strain was estimated by determination of acidity and pH.

The results are set forth in Table 3.

TABLE 3

| | Condition of the Broth after Incubation | |
|---|---|---|
| Test medium | Acidity | pH |
| Standard Medium Containing the Product of the Invention | 0.66 | 5.0 |
| Standard Medium Containing the Untreated Mixture | 0.28 | 5.5 |
| Standard Medium | 0.23 | 5.8 |

It is apparent from Table 3 that the product of this invention has bifidus activity.

The immobilized yeast cell preparation obtained above was used in the production of bifidus factor under the same conditions for a total of 10 times but there was no decrease in bifidus factor-synthesizing activity.

EXAMPLE 13

To 200 g of lactose was added 10 g, on a dry basis, of the moist cells of Lipomyces NKD-14 (FERM P-8948) obtained in Reference Example 13 followed by addition of tap water to make 1 liter. This reaction mixture was maintained at 30° C. and pH 6.5 for 6 days.

After completion of the reaction, the supernatant was taken and analyzed in the same manner as Example 1. As a result, a peak of galacto-oligosaccharide was detected at the trisaccharide position as well as the peak of substrate lactose.

In this condition, the concentration of lactose was 6.6% and that of galacto-oligosaccharide was 10.0%. The yield of galacto-oligosaccharide relative to the starting material lactose was 50%.

Glucose and galactose, which are hydrolysates of lactose, were not detected at all. It was clear that galacto-oligosaccharide could be produced without formation of by-products.

Then, in order to isolate the galacto-oligosaccharide alone, the supernatant of the reaction mixture was passed through a column of activated carbon, whereby 85 g of galacto-oligosaccharide was obtained. This galacto-oligosaccharide gave a single peak on the high performance liquid chromatography (HPLC) under the conditions described hereinbefore. Structural analysis of this product by $^{13}$C NMR revealed that it was O-βD-galactopyranosyl-(1→4)-O-β-D-galactopyranosyl-(1→4)-D-glucose.

EXAMPLE 14

A column was packed with 80 g of the immobilized cells obtained in reference Example 14 and 200 ml of 30% lactose was circulated through the column. The 5-day reaction at pH 6.5 and 40° C. yielded 13.5% of galacto-oligosaccharide.

Neither glucose nor galactose was detected.

The 5-day reaction was carried out for a total of 10 times but there was no decrease in enzymatic activity.

EXAMPLE 15

In 4 ml of physiological saline was suspended 1 g of the moist cells of Lipomyces NKD-14 (FERM P-8948) obtained in Reference Example 15 followed by addition of 750 mg of acrylamide and, as a crosslinking agent, 40 mg of N,N'-methylenebisacrylamide. Then, 0.5 ml of 5% β-dimethylaminopropionitrile as a polymerization accelerator and 0.5 ml of 2.5% potassium peroxydisulfate as a polymerization initiator were added. The mixture was stirred well and allowed to stand at 30° C. for 30 days. The resulting gel was washed with physiological saline to give an immobilized yeast cell preparation.

To this immobilized yeast cell preparation was added 1 g of lactose followed by addition of tap water to make 10 ml. The reaction was conducted at pH 6.0 and 40° C. for 3 days.

Then, the supernatant of the reaction mixture was analyzed in the same manner as Example 1. As a result, galacto-oligosaccharide was detected in a yield of 5.2%. Neither glucose nor galactose was detected. The yield of galacto-oligossaccharide based on lactose was 52%.

While the invention has been described in detail and with reference to specific embodiments thereof, it will be apparent to one skilled in the art that various changes and modifications can be made therein without departing from the spirit and scope thereof.

What is claimed is:

1. A method of producing a growth promoting factor for Bifidobacterium species from lactose which comprises contacting lactose with resting cells of a lactose-utilizing yeast strain having activity to rearrange lactose to galacto-oligosaccharides and which is a member selected from the group consisting of Rhodotorula lactosa, Pichia polymorpha, Kluyveromyces lactis, Debaryomyces cantarellii, Candida curvata, Torulopsis candida, Trichosporon pullulans, Lipomyces lipofer, Bullera alba, and Brettanomyces anomalus.

2. The method of claim 1, wherein said lactose-utilizing yeast strain is a strain of the genus Rhodotorula lactosa.

3. The method of claim 1, wherein said lactose-utilizing yeast strain is a strain of the genus Pichia polymorpha.

4. The method of claim 1, wherein said lactose-utilizing yeast strain is a strain of the genus Kluyveromyces lactis.

5. The method of claim 1, wherein said lactose-utilizing yeast strain is a strain of the genus Debaryomyces cantarellii.

6. The method of claim 1, wherein said lactose-utilizing yeast strain is a strain of the genus Candida curvata.

7. The method of claim 1, wherein said lactose-utilizing yeast strain is a strain of the genus Torulopsis candida.

8. The method of claim 1, wherein said lactose-utilizing yeast strain is a strain of the genus Trichosporon pullulans.

9. The method of claim 1, wherein said lactose-utilizing yeast strain is a strain of the genus Lipomyces lipofer.

10. The method of claim 1, wherein said lactose-utilizing yeast strain is a strain of the genus Bullera alba.

11. The method of claim 1, wherein said lactose-utilizing yeast strain is a strain of the genus Brettanomyces anomalus.

12. The method of claim 1, wherein said resting cells of a lactose-utilizing yeast strain are immobilized yeast cells.

13. A method of producing a growth promoting factor for Bifidobacterium species from lactose which comprises contacting lactose with resting cells of a lactose-utilizing yeast strain having activity to rearrange lactose to galacto-oligosaccharides, wherein said yeast strain is Lipomyces NKD-14 (FERM UP-1456).

14. A method according to claim 12, wherein said resting cells of a lactose utilizing yeast strain are immobilized yeast cells.

* * * * *